United States Patent
Boutillette et al.

(10) Patent No.: US 10,058,236 B2
(45) Date of Patent: Aug. 28, 2018

(54) FIBER OPTIC IMAGING CATHETER

(71) Applicant: Boston Scientific Scimed, Inc., Maple Grove, MN (US)

(72) Inventors: Michael P. Boutillette, San Francisco, CA (US); Paul M. Scopton, Winchester, MA (US); David Micky Graves, Mesa, AZ (US); Kevin M. Richardson, Austin, TX (US); David I. Freed, Westborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 195 days.

(21) Appl. No.: 14/945,817

(22) Filed: Nov. 19, 2015

(65) Prior Publication Data
US 2016/0073857 A1    Mar. 17, 2016

Related U.S. Application Data

(63) Continuation of application No. 14/055,580, filed on Oct. 16, 2013, now Pat. No. 9,215,970, which is a
(Continued)

(51) Int. Cl.
*A61B 1/00* (2006.01)
*A61B 1/04* (2006.01)
(Continued)

(52) U.S. Cl.
CPC .......... *A61B 1/0057* (2013.01); *A61B 1/0051* (2013.01); *A61B 1/0052* (2013.01);
(Continued)

(58) Field of Classification Search
CPC .......... A61B 1/0057; A61B 1/07; A61B 1/05; A61B 1/00096; A61B 1/018;
(Continued)

(56) References Cited

U.S. PATENT DOCUMENTS

| | | |
|---|---|---|
| 3,572,325 A | 3/1971 | Bazell et al. |
| 3,573,325 A | 3/1971 | Thominet |

(Continued)

FOREIGN PATENT DOCUMENTS

| | | |
|---|---|---|
| EP | 0 754 429 A2 | 1/1997 |
| EP | 0 815 895 A1 | 1/1998 |

(Continued)

OTHER PUBLICATIONS

Satyanarayanan, "Fundamental Challenges in Mobile Computing," School of Computer Science, Carnegie Mellon University, 7 pp.
(Continued)

*Primary Examiner* — Timothy J Neal
(74) *Attorney, Agent, or Firm* — Bookoff McAndrews, PLLC

(57) ABSTRACT

A steerable imaging catheter is provided, including an elongated catheter tube, at least one steering cable extending along the catheter tube to control the movement of the distal end thereof, and a fiber optic cable extending along the catheter tube. The fiber optic cable transmits illumination light from its proximal end to its distal end and transmits an image from its distal end to its proximal end. In one embodiment, two or more steering cables are used, and the catheter tube is configured to have greater flexibility near its distal end than its proximal end so as to concentrate the movement (flexing) of the catheter tube at its distal end. The use of two or more steering cables, together with the catheter tube having varying flexibility, permit better control of the distal end of the catheter tube while reducing undue twisting of the remainder of the catheter tube.

4 Claims, 3 Drawing Sheets

Related U.S. Application Data continuation of application No. 13/041,520, filed on Mar. 7, 2011, now abandoned, which is a continuation of application No. 10/914,411, filed on Aug. 9, 2004, now Pat. No. 7,922,654.

(51) Int. Cl.

| | | |
|---|---|---|
| *A61B 1/005* | (2006.01) | |
| *A61B 1/015* | (2006.01) | |
| *A61B 1/06* | (2006.01) | |
| *A61B 1/07* | (2006.01) | |
| *A61B 1/018* | (2006.01) | |
| *A61B 1/05* | (2006.01) | |
| A61B 90/00 | (2016.01) | |
| A61B 90/30 | (2016.01) | |

(52) U.S. Cl.
CPC ...... *A61B 1/00071* (2013.01); *A61B 1/00096* (2013.01); *A61B 1/00103* (2013.01); *A61B 1/00135* (2013.01); *A61B 1/00165* (2013.01); *A61B 1/015* (2013.01); *A61B 1/018* (2013.01); *A61B 1/04* (2013.01); *A61B 1/05* (2013.01); *A61B 1/0607* (2013.01); *A61B 1/07* (2013.01); *A61B 2090/061* (2016.02); *A61B 2090/306* (2016.02); *A61B 2090/3614* (2016.02); *A61B 2090/3937* (2016.02)

(58) Field of Classification Search
CPC .............. A61B 1/0071; A61B 1/00135; A61B 1/00165; A61B 1/0051; A61B 1/0052; A61B 1/0125; A61B 1/00167; A61B 1/0017

See application file for complete search history.

(56) References Cited

U.S. PATENT DOCUMENTS

| | | | |
|---|---|---|---|
| 3,886,933 A | | 6/1975 | Mori et al. |
| 3,913,568 A | | 10/1975 | Carpenter |
| 3,941,121 A | | 3/1976 | Olinger et al. |
| 4,027,510 A | | 6/1977 | Hiltebrandt |
| 4,325,374 A | | 4/1982 | Komiya |
| 4,461,282 A | | 7/1984 | Ouchi et al. |
| 4,586,491 A | * | 5/1986 | Carpenter .......... A61B 1/00165 600/106 |
| 4,660,560 A | | 4/1987 | Klein |
| 4,782,819 A | | 11/1988 | Adair |
| 4,784,144 A | | 11/1988 | Ono et al. |
| 4,790,295 A | | 12/1988 | Tashiro |
| 4,800,870 A | | 1/1989 | Reid |
| 4,802,460 A | | 2/1989 | Ohkuwa et al. |
| 4,802,461 A | | 2/1989 | Cho |
| 4,807,595 A | | 2/1989 | Hiltebrandt |
| 4,834,069 A | | 5/1989 | Umeda |
| 4,882,727 A | | 11/1989 | Williams et al. |
| 4,899,723 A | | 2/1990 | Pajares |
| 4,905,667 A | | 3/1990 | Foerster et al. |
| 4,911,148 A | | 3/1990 | Sosnowski et al. |
| 4,921,326 A | | 5/1990 | Wild et al. |
| 4,945,894 A | | 8/1990 | Kawashima |
| 4,979,496 A | | 12/1990 | Komi |
| 4,982,725 A | | 1/1991 | Hibino et al. |
| 5,009,655 A | | 4/1991 | Daignault, Jr. et al. |
| 5,014,685 A | | 5/1991 | Takahashi |
| 5,035,696 A | | 7/1991 | Rydell |
| 5,047,627 A | | 9/1991 | Yim et al. |
| 5,098,659 A | | 3/1992 | Yim et al. |
| 5,114,402 A | | 5/1992 | McCoy |
| 5,163,927 A | | 11/1992 | Woker et al. |
| 5,178,130 A | | 1/1993 | Kaiya |
| 5,199,950 A | | 4/1993 | Schmitt et al. |
| 5,273,535 A | | 12/1993 | Edwards et al. |
| 5,299,560 A | * | 4/1994 | Hatori .............. A61B 1/00165 385/117 |
| 5,311,858 A | | 5/1994 | Adair |
| 5,325,845 A | | 7/1994 | Adair |
| 5,342,299 A | | 8/1994 | Snoke et al. |
| 5,368,564 A | | 11/1994 | Savage |
| 5,376,094 A | | 12/1994 | Kline |
| 5,379,779 A | | 1/1995 | Rowland et al. |
| 5,383,467 A | | 1/1995 | Auer et al. |
| 5,396,880 A | | 3/1995 | Kagan et al. |
| 5,403,311 A | | 4/1995 | Abele et al. |
| 5,409,453 A | | 4/1995 | Lundquist et al. |
| 5,412,749 A | | 5/1995 | Sayegh et al. |
| 5,415,158 A | | 5/1995 | Barthel et al. |
| 5,423,003 A | | 6/1995 | Berteau |
| 5,439,000 A | | 8/1995 | Gunderson et al. |
| D363,544 S | | 10/1995 | Rowland et al. |
| D363,776 S | | 10/1995 | Rowland et al. |
| 5,456,245 A | * | 10/1995 | Bornhop ............. A61B 1/042 385/117 |
| 5,478,338 A | | 12/1995 | Reynard |
| 5,531,687 A | | 7/1996 | Snoke et al. |
| 5,546,577 A | | 8/1996 | Marlin et al. |
| 5,569,161 A | | 10/1996 | Ebling et al. |
| 5,601,087 A | | 2/1997 | Gunderson et al. |
| 5,624,397 A | | 4/1997 | Snoke et al. |
| 5,647,840 A | | 7/1997 | D'Amelio et al. |
| 5,667,472 A | | 9/1997 | Finn et al. |
| 5,680,615 A | | 10/1997 | Marlin et al. |
| 5,702,754 A | | 12/1997 | Zhong |
| 5,733,242 A | | 3/1998 | Rayburn et al. |
| 5,746,692 A | | 5/1998 | Bacich et al. |
| 5,758,074 A | | 5/1998 | Marlin et al. |
| 5,778,377 A | | 7/1998 | Marlin et al. |
| 5,779,643 A | | 7/1998 | Lum et al. |
| 5,803,898 A | | 9/1998 | Bashour |
| 5,824,026 A | | 10/1998 | Diaz |
| 5,860,914 A | | 1/1999 | Chiba et al. |
| 5,867,714 A | | 2/1999 | Todd et al. |
| 5,879,287 A | | 3/1999 | Yoshihashi |
| 5,910,129 A | | 6/1999 | Koblish et al. |
| 5,926,636 A | | 7/1999 | Lam et al. |
| 5,928,137 A | | 7/1999 | Green |
| 5,938,588 A | | 8/1999 | Grabover et al. |
| 5,960,145 A | | 9/1999 | Sanchez |
| 5,961,599 A | | 10/1999 | Kalavade et al. |
| 5,968,116 A | | 10/1999 | Day, II et al. |
| 5,976,129 A | | 11/1999 | Desai |
| 5,991,806 A | | 11/1999 | McHann, Jr. |
| 5,993,378 A | | 11/1999 | Lemelson |
| 5,993,447 A | | 11/1999 | Blewett et al. |
| 6,007,522 A | | 12/1999 | Agro et al. |
| 6,007,531 A | | 12/1999 | Snoke et al. |
| 6,012,100 A | | 1/2000 | Frailong et al. |
| 6,013,025 A | | 1/2000 | Bonne et al. |
| 6,017,322 A | | 1/2000 | Snoke et al. |
| 6,021,445 A | | 2/2000 | Chapa |
| 6,026,354 A | | 2/2000 | Singh et al. |
| 6,038,611 A | | 3/2000 | Masel |
| 6,044,408 A | | 3/2000 | Engstrom et al. |
| 6,048,620 A | | 4/2000 | Zhong |
| 6,052,727 A | | 4/2000 | Kamalanathan |
| 6,055,562 A | | 4/2000 | Devarakonda et al. |
| 6,081,740 A | | 6/2000 | Gombrich et al. |
| 6,096,009 A | | 8/2000 | Windheuser et al. |
| 6,126,633 A | | 10/2000 | Kaji et al. |
| 6,174,291 B1 | | 1/2001 | McMahon et al. |
| 6,203,494 B1 | | 3/2001 | Moriyama |
| 6,228,032 B1 | | 5/2001 | Eaton et al. |
| 6,277,064 B1 | | 8/2001 | Yoon |
| 6,296,608 B1 | | 10/2001 | Daniels et al. |
| 6,328,730 B1 | | 12/2001 | Harkrider |
| 6,349,357 B1 | | 2/2002 | Chong, Jr. |
| 6,350,234 B1 | | 2/2002 | Foerster-Klein et al. |
| 6,397,259 B1 | | 5/2002 | Lincke et al. |
| 6,398,776 B1 | | 6/2002 | Sekino et al. |
| 6,400,157 B1 | | 6/2002 | Bonanni et al. |
| 6,442,611 B1 | | 8/2002 | Navarre et al. |
| 6,544,215 B1 | | 4/2003 | Bencini et al. |

(56) References Cited

U.S. PATENT DOCUMENTS

| | | |
|---|---|---|
| 6,554,766 B2 | 4/2003 | Maeda et al. |
| 6,589,163 B2 | 7/2003 | Aizama et al. |
| 6,626,824 B2 | 9/2003 | Ruegg et al. |
| 6,654,630 B2 | 11/2003 | Zuluaga et al. |
| 6,673,012 B2 | 1/2004 | Fujii et al. |
| 6,702,750 B2 | 3/2004 | Yock |
| 6,752,800 B1 | 6/2004 | Winston et al. |
| 6,796,939 B1 | 9/2004 | Hirata et al. |
| 6,814,698 B2 | 11/2004 | Barthel et al. |
| 6,837,849 B2 | 1/2005 | Ogura et al. |
| 6,966,906 B2 | 11/2005 | Brown |
| 6,979,290 B2 | 12/2005 | Mourlas et al. |
| 6,994,667 B2 | 2/2006 | Singh |
| 7,198,599 B2 | 4/2007 | Goto et al. |
| 7,223,230 B2 | 5/2007 | Zirps et al. |
| 7,232,434 B2 | 6/2007 | Suyama et al. |
| 7,235,043 B2 | 6/2007 | Gellman et al. |
| 7,413,543 B2 | 8/2008 | Banik et al. |
| 7,615,032 B2 | 11/2009 | Whittaker et al. |
| 7,662,089 B2 | 2/2010 | Okada et al. |
| 7,914,441 B2 | 3/2011 | Otawara |
| 7,922,654 B2 | 4/2011 | Boutillette et al. |
| 2002/0013532 A1 | 1/2002 | Czubko et al. |
| 2002/0026188 A1 | 2/2002 | Balbierz et al. |
| 2002/0068851 A1 | 6/2002 | Gravenstein et al. |
| 2002/0087047 A1 | 7/2002 | Remijan et al. |
| 2002/0111548 A1 | 8/2002 | Swanson et al. |
| 2002/0115983 A1 | 8/2002 | Sekino et al. |
| 2002/0168317 A1 | 11/2002 | Daighighian et al. |
| 2002/0188177 A1 | 12/2002 | Miyanaga |
| 2002/0188285 A1 | 12/2002 | Brown |
| 2003/0004460 A1 | 1/2003 | Bedell |
| 2003/0028200 A1 | 2/2003 | Berg et al. |
| 2003/0078475 A1 | 4/2003 | Hirata et al. |
| 2003/0083552 A1 | 5/2003 | Remijan et al. |
| 2003/0088153 A1* | 5/2003 | Carrillo, Jr. ........ A61M 25/0075 600/114 |
| 2003/0153813 A1 | 8/2003 | Kasel et al. |
| 2003/0212308 A1 | 11/2003 | Bendall |
| 2003/0216616 A1 | 11/2003 | Krupa et al. |
| 2004/0015050 A1 | 1/2004 | Goto et al. |
| 2004/0052679 A1 | 3/2004 | Root et al. |
| 2004/0077950 A1 | 4/2004 | Marshik-Geurts et al. |
| 2004/0116800 A1 | 6/2004 | Helfer et al. |
| 2004/0172052 A1 | 9/2004 | Fogarty et al. |
| 2004/0199052 A1 | 10/2004 | Banik et al. |
| 2004/0220449 A1 | 11/2004 | Zirps et al. |
| 2004/0225187 A1 | 11/2004 | Kamrava et al. |
| 2004/0254422 A1 | 12/2004 | Singh |
| 2005/0165288 A1 | 7/2005 | Rioux et al. |
| 2005/0177024 A1 | 8/2005 | Mackin |
| 2005/0182292 A1 | 8/2005 | Suzuki |
| 2005/0192480 A1 | 9/2005 | Toriya et al. |
| 2005/0278010 A1 | 12/2005 | Richardson |
| 2006/0089660 A1 | 4/2006 | Saeed et al. |
| 2006/0149129 A1 | 7/2006 | Watts et al. |
| 2006/0252993 A1 | 11/2006 | Freed et al. |
| 2006/0258955 A1 | 11/2006 | Hoffman et al. |
| 2008/0064925 A1 | 3/2008 | Gill et al. |
| 2008/0097159 A1 | 4/2008 | Ishiguro |
| 2010/0198009 A1 | 8/2010 | Farr et al. |

FOREIGN PATENT DOCUMENTS

| | | |
|---|---|---|
| EP | 1 302 151 A2 | 4/2003 |
| EP | 1 502 537 A1 | 2/2005 |
| EP | 1 568 305 A1 | 8/2005 |
| EP | 1 842 499 A1 | 10/2007 |
| JP | 04-354926 | 12/1992 |
| JP | 3004466 | 11/1994 |
| JP | 8-501949 | 3/1996 |
| JP | 10-057500 | 3/1998 |
| JP | 11-313827 | 11/1999 |
| JP | 2000-121962 | 4/2000 |
| JP | 2000-157486 | 6/2000 |
| JP | 2002-521114 | 7/2002 |
| JP | 2002-272675 | 9/2002 |
| JP | 2004-049891 | 2/2004 |
| JP | 2004-503339 | 2/2004 |
| JP | 2004-533864 | 11/2004 |
| JP | 2005-052630 | 3/2005 |
| JP | 2005-514992 | 5/2005 |
| JP | 2005-169012 | 6/2005 |
| JP | 2006-015017 | 1/2006 |
| JP | 2007-535972 | 12/2007 |
| WO | WO 91/11213 | 8/1991 |
| WO | WO 94/01162 | 1/1994 |
| WO | WO 94/11040 | 5/1994 |
| WO | WO 97/29679 | 8/1997 |
| WO | WO 99/40432 | 8/1999 |
| WO | WO 99/45847 | 9/1999 |
| WO | WO 00/06013 | 2/2000 |
| WO | WO 01/56457 | 8/2001 |
| WO | WO 01/78825 | 10/2001 |
| WO | WO 01/89598 | 11/2001 |
| WO | WO 02/05885 | 1/2002 |
| WO | WO 03/059429 | 7/2003 |
| WO | WO 03/082394 | 10/2003 |
| WO | WO 2004/007012 | 1/2004 |
| WO | WO 2004/012805 | 2/2004 |
| WO | WO 2006/004053 | 1/2006 |

OTHER PUBLICATIONS

Duchamp, "Issues in Wireless Mobile Computing," Computer Science Department, Columbia University, 7 pp. (unnumbered).

de Lara et al., "Opportunities for Bandwidth Adaptation in Microsoft Office Documents," Department of Electrical and Computer Engineering, Department of Computer Science, Rice University, 12 pp. (unnumbered).

de Lara et al., "Puppeteer: Component-based Adaptation for Mobile Computing," Department of Electrical and Computer Engineering, Department of Computer Science, Rice University, 12 pp.

Noble et al., "A Research Status Report on Adaptation for Mobile Data Access," School of Computer Science, Carnegie Mellon University, 6 pp. (unnumbered).

Joseph et al., "Rover: A toolkit for Mobile Information Access," appears in Proceedings of the Fifteenth Symposium on Operating Systems Principles, Dec. 1995, 16 pp.

Andersen et al., "System Support for Bandwidth Management and Content Adaptation in Internet Applications," M.I.T. Laboratory for Computer Science, 14 pp. (unnumbered).

Bagrodia et al., "Vision, Issues, and Architecture for Nomadic Computing," 27 pp.

Satyanarayanan et al., "Visual Proxy: Exploiting OS Customizations without Application Source Code," School of Computer Science, Carnegie Mellon University, 5 pp.

Katz, "Adaptation and Mobility in Wireless Information Systems," IEEE Personal Communications, First Quarter 1994, pp. 6-17.

Fox et al., "Adapting to Network and Client Variability via On-Demand Dynamic Distillation," University of California at Berkeley, pp. 1-11.

Fox et al., "Adapting to Network and Client Variation Using Infrastructural Proxies: Lessons and Perspectives," University of California at Berkeley, 15 pp. (unnumbered).

Noble et al., "Agile Application-Aware Adaptation for Mobility," to appear in the Proceedings of the 16th ACM Symposium on Operating System Principles, School of Computer Science, Carnegie Mellon University, 12 pp. (unnumbered).

Joseph et al., "Building Reliable Mobile-Aware Applications using the Rover Toolkit," appears in Proceedings of the 2nd ACM International Conference on Mobile Computing and Networking, Nov. 1996, 13 pp. (unnumbered).

Forman et al., "The Challenges of Mobile Computing," University of Washington, available as UW CSE Tech Report # 93-11-03 from ftp.cs.washington.edu (16 pp). An edited version of this paper has been accepted for publication in IEEE Computer.

(56) References Cited

OTHER PUBLICATIONS

Cunha et al., "Characteristics of WWW Client-based Traces," Computer Science Department, Boston University, BU-CS-95-010, Jul. 18, 1995, 18 pp.

Kistler et al., "Disconnected Operation in the Coda File System," ACM Transactions on Computer Systems, vol. 10, No. 1, Feb. 1992, pp. 3-25.

Kaashoek et al., "Dynamic Documents: Mobile Wireless Access to the WWW," MIT Laboratory for Computer Science, to appear in Proceedings of the IEEE Workshop on Mobile Computing Systems and Applications, Santa Cruz, CA, Dec. 1994, 6 pp.

Mummert et al., "Exploiting Weak Connectivity for Mobile File Access," Carnegie Mellon University, SIGOPS '95 Dec. 1995 CO, USA, pp. 143-155.

Myers et al., "Extending the Windows Desktop Interface With Connected Handheld Computers," Human Computer Interaction Institute, School of Computer Science, Carnegie Mellon University, submitted for publication, pp. 1-10.

A communication from the Japanese Patent Office citing the above Japanese Patents in Patent Application No. 2007-505103, dated Nov. 10, 2009.

An English language version of a communication from the Japanese Patent Office citing the above Japanese Patents in Patent Application No. 2007-505103, dated Mar. 29, 2010.

A communication from the Japanese Patent Office citing the above Japanese Patents in Patent Application No. 2007-525748, dated Aug. 10, 2011.

\* cited by examiner

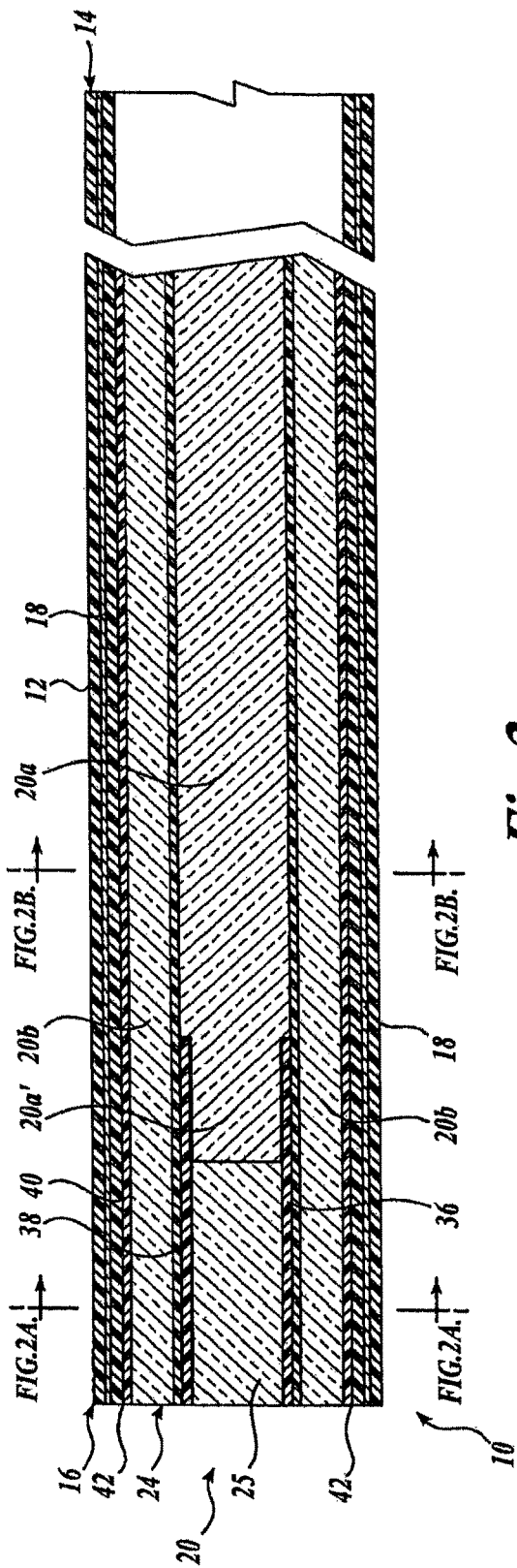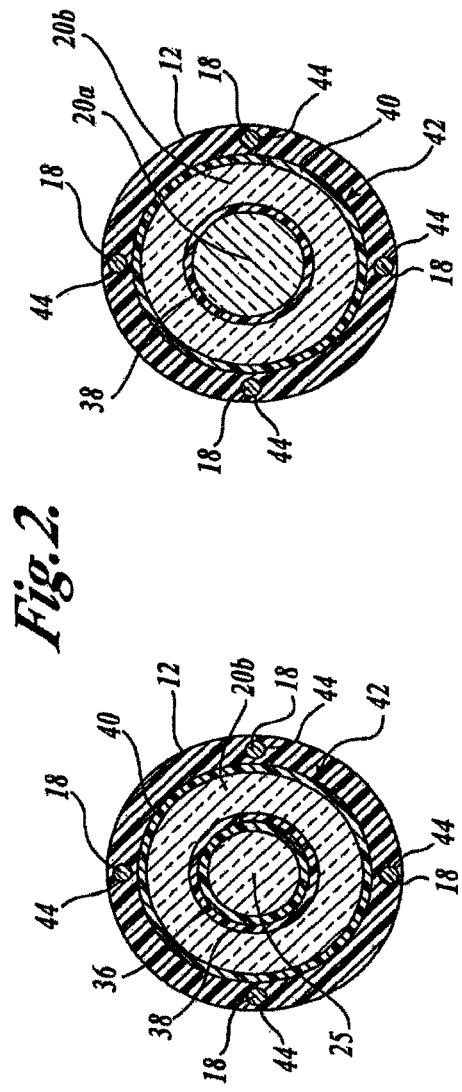
Fig. 2.
Fig. 2A.
Fig. 2B.

ns. No. 14/055,580, filed Oct. 16, 2013, now U.S. Pat.
FIBER OPTIC IMAGING CATHETER This application is a continuation of U.S. patent application Ser. No. 14/055,580, filed Oct. 16, 2013, now U.S. Pat. No. 9,215,970, which is a continuation of U.S. patent application Ser. No. 13/041,520, filed Mar. 7, 2011, now abandoned, which is a continuation of U.S. patent application Ser. No. 10/914,411, filed Aug. 9, 2004, now U.S. Pat. No. 7,922,654, all of which are herein incorporated by reference in their entireties.

FIELD OF THE INVENTION

The present invention relates to medical devices, and in particular to a fiber optic catheter with imaging capabilities.

BACKGROUND OF THE INVENTION

An endoscope is a piece of surgical equipment that has imaging capabilities so as to be able to provide images of an internal body cavity of a patient. Most minimally invasive surgical procedures performed in the gastrointestinal (GI) tract or other internal body cavities are accomplished with the aid of an endoscope. An endoscope includes one or more working channels through which other medical catheters/instruments can pass. Typically, an endoscope is used to reach an area of interest within a body cavity and, thereafter, another instrument such as a surgical catheter is extended through the working channel of the endoscope to perform some desired procedure. An endoscope, however, typically has a diameter that is relatively large with respect to the body cavity or body lumen through which it must pass.

A need exists for smaller-diameter devices with imaging capability. Preferably, such smaller-diameter devices are steerable so that a physician can readily obtain an image of a location of interest within the body cavity.

SUMMARY OF THE INVENTION

The present invention is a smaller-diameter device with imaging capability involving a single optical fiber or an optical fiber bundle. In one embodiment, an optical fiber or fiber bundle with imaging capability is received axially through a lumen of a steerable catheter. Such a catheter typically includes a single steering cable, a distal end of which is attached to the distal end of the catheter. By manipulating the proximal end of the steering cable, a physician can bend the distal end of the catheter to thereby steer the catheter. A steerable catheter with a single steering cable, however, can bend only in one direction. Thus, to bend the catheter in any desired direction in a three-dimensional space, the catheter must be axially rotated so that the one-directional bend will point in the desired direction. Consequently, the steerable catheter incorporating an optical fiber is subjected to repeated torque that twists and potentially damages the fiber.

To overcome the foregoing disadvantage in some applications, the present invention further offers a steerable imaging catheter including a fiber optic cable, which is configured to minimize the application of undesirable torque to the fiber optic cable. To achieve this goal, in one embodiment, a steerable imaging catheter uses at least two cables that bend and steer the catheter. The use of multiple steering cables reduces the need for axially rotating the catheter to achieve a desired bend, and therefore minimizes unduly twisting and damaging the fiber optic cable. In another embodiment of the present invention, a steerable imaging catheter is formed of a catheter tube that has greater flexibility near its distal end portion and has greater stiffness (column strength) in the remainder of the tube. This construction concentrates any flexing and also some torque application at the distal end portion of the tube, while minimizing undue twisting of the tube including the fiber optic cable in the remainder of the tube.

Specifically, according to one embodiment of the present invention, a steerable imaging catheter is provided, including an elongated catheter tube, at least two steering cables extending along the catheter tube to control the movement of the distal end of the catheter tube, and a fiber optic cable extending through the catheter tube. The catheter may be an imaging-only catheter whose sole function is imaging, or may be any diagnostic/therapeutic catheter having a diagnostic/therapeutic function (e.g., a balloon catheter, stent delivery catheter, sphincterotomy catheter, etc.) in addition to the imaging function. The fiber optic cable transmits illumination light from its proximal end to its distal end and further transmits an image from its distal end to its proximal end. The diameter of the steerable imaging catheter is generally between 1 mm and 4.5 mm, which is smaller than that of a conventional endoscope to permit visualization of a body cavity/lumen that typically cannot be reached by an endoscope. The use of multiple steering cables to control the distal end of the catheter tube permits bending of the distal end in various (two or more) directions in varying degrees. This feature not only prevents undue twisting of the fiber optic cable, but also adds to the maneuverability of the catheter tube, and further significantly increases the range of view of the fiber optic cable.

According to another embodiment of the present invention, a steerable imaging catheter is provided, including an elongated catheter tube, at least one steering cable extending along the catheter tube to control the movement of the distal end of the catheter tube, and a fiber optic cable extending through the catheter tube. As before, the catheter may be an imaging-only catheter whose sole function is imaging, or may be any diagnostic/therapeutic catheter having a diagnostic/therapeutic function in addition to the imaging function. The catheter tube is constructed so as to have greater flexibility near its distal end portion while having greater stiffness in the remainder of the tube. This may be accomplished, for example, by varying the durometer rating of the materials used to form the catheter tube. Such construction concentrates the flexing at the distal end portion, rather than throughout the entire catheter tube, to thereby reduce undue twisting of the catheter tube along its entire length, and further to permit better control of the movement of the distal end portion.

According to one embodiment of the invention, a catheter tube defines a plurality of lumens extending therethrough, and one of the lumens receives the fiber optic cable. The other lumens may receive irrigation/sufflation fluid or other devices or equipment. In one embodiment, the other lumen may receive a measuring probe therethrough. The measuring probe includes incremental or numerical markings provided at its distal end portion. By placing the incremental markings and an object to be measured in the field of view of the fiber optic cable, a physician can visually measure the size of the object in reference to the incremental markings.

According to another embodiment of the invention, the other lumen may receive a cutting device such as a cutting wire for delivering RF energy. A physician can deliver the cutting wire and the fiber optic cable through the catheter tube into the body cavity, observe any undesirable material (tissue, stone, etc.) using the fiber optic cable, and then deploy the cutting wire to deliver RF energy to the undesirable material to cut it out while observing the cut-out operation using the fiber optic cable.

According to another embodiment of the invention, the fiber optic cable and/or the catheter tube are coated with hydrophilic material.

According to yet another embodiment of the invention, the fiber optic cable may be used to carry out an optical diagnostic/treatment procedure, such as an optical biopsy.

According to still another embodiment of the invention, the fiber optic cable is integrally formed with the catheter tube.

According to a further embodiment of the invention, the catheter tube is configured to be separable from the fiber optic cable so as to be discarded after each use, while the fiber optic cable may be retained for reuse.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2 is a cross sectional view of a catheter tube of a steerable imaging catheter formed in accordance with the present invention;

FIGS. 2A and 2B are radial cross sectional views cut along lines A-A and B-B, respectively, of FIG. 2;

DETAILED DESCRIPTION OF THE PREFERRED EMBODIMENT

Figure 1:
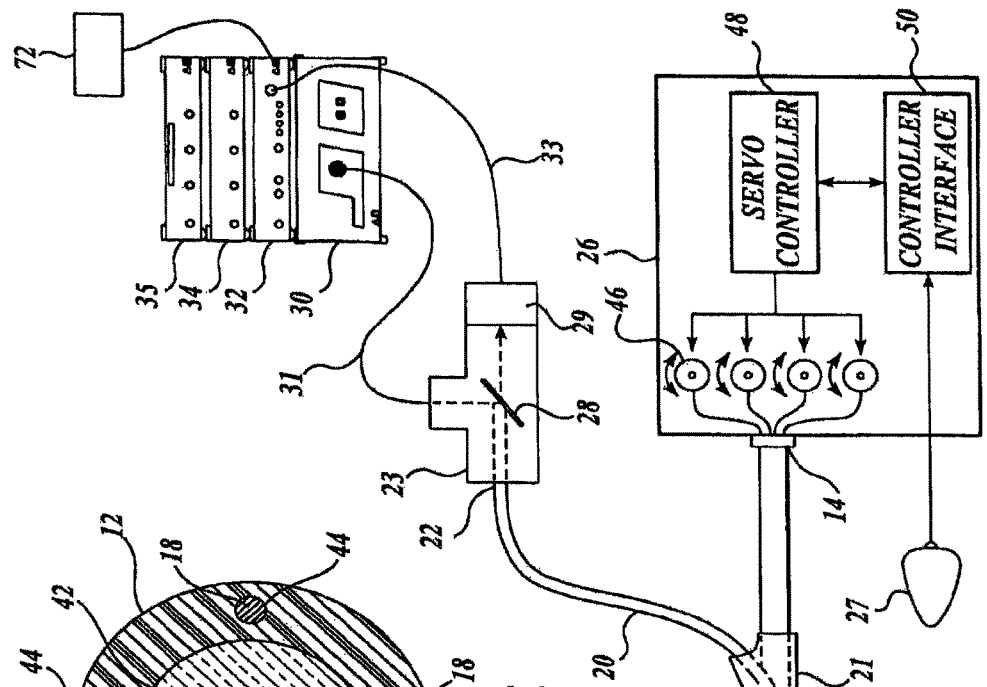
FIG. 1 is a block diagram illustrating a steerable imaging catheter formed in accordance with the present invention together with related equipment.
Figure 3:
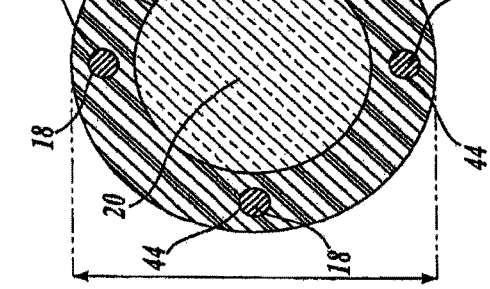
FIG. 3 is a radial cross sectional view of a catheter tube including four steering cables, formed in accordance with an embodiment of the present invention.

FIGS. 1-3 illustrate a steerable imaging catheter 10 formed in accordance with the present invention. The catheter 10 includes an elongated catheter tube 12 having a proximal end 14 and a distal end 16. The catheter 10 may be an imaging-only catheter, whose sole function is imaging, or may be any diagnostic/therapeutic catheter having some diagnostic/therapeutic function in addition to the imaging function (e.g., a balloon catheter, stent delivery catheter, sphincterotomy catheter, etc.). Referring specifically to FIGS. 2, 2A, 2B, and 3, four steering cables 18 are positioned at equal distances around the circumference of the catheter tube 12, and extend along the length of the catheter tube 12 substantially from the proximal end 14 to the distal end 16. The steering cables 18 of the catheter tube 12 control the movement of the distal end 16 of the catheter tube. The catheter 10 also includes a fiber optic cable 20 having a proximal end 22 and a distal end 24, which extends at least partially along the length of the catheter tube 12. To this end, the illustrated embodiment as shown in FIG. 1 includes a breakout unit 21 configured to receive and combine the catheter tube 12 and the fiber optic cable 20. As will be apparent, in this embodiment, an outer wall of the catheter tube 12 includes an opening 19 through which the fiber optic cable 20 enters into the catheter tube 12 so as to extend through and within the catheter tube 12. The fiber optic cable 20 is configured to transmit illumination light from its proximal end 22 to the distal end 24, and also to transmit an image from its distal end 24 to the proximal end 22. In the illustrated embodiment, as best shown in FIG. 2, the fiber optic cable 20 includes one or more centrally extending coherent imaging fibers 20a and one or more circumferentially extending illumination fibers 20b (which may not be coherent) that generally surround the one or more imaging fibers 20a. Further, an objective lens 25 is attached to the distal end of the one or more imaging fibers 20a.

Referring specifically to FIG. 1, the four steering cables 18 are coupled to a control housing 26, from which a handheld controller 27 extends. The control housing 26 includes a number of actuators coupled to the proximal ends of the steering cables 18. An operator can manipulate the steering cables 18 using control signals generated by the handheld controller 27 to steer the distal end 16 of the catheter tube 12 in order to maneuver the catheter 10 through a body cavity.

Still referring to FIG. 1, the proximal end 22 of the fiber optic cable 20 may be connected to an eyepiece 23. The eyepiece 23 includes a light splitter 28 and a camera (or image sensor) 29. The light splitter 28 receives illumination light from a light source 30 through a cable 31. The cable 31 may include a group of standard clad optical fibers that function as illumination fibers for carrying the illumination light from the light source 30 to the light splitter 28. The light from the light splitter 28 is coupled to the one or more illumination fibers 20b in the fiber optic cable 20 for delivery to the distal end 24 thereof in order to illuminate the imaged area. An image from the distal end 24 of the fiber optic cable 20 is transmitted through the one or more imaging fibers 20a in the fiber optic cable 20 to the proximal end 22 thereof, and through the light splitter 28 within the eyepiece 23 to the camera (or image sensor) 29. The image is then processed and supplied from the camera (or image sensor) 29 via a cable 33 to a camera control unit 32 coupled to a display (not shown) that displays an image of the viewed area. Additionally, the eyepiece 23 permits direct visualization of the viewed area. Still further, a picture-in-picture unit 34 and a DVD recorder 35 may be provided to allow a physician to view more than one image at a time on the display as well as to record images for future review.

FIG. 2 illustrates an embodiment of a fiber optic cable 20 suitable for use in the present invention. In the illustrated embodiment, the objective lens 25 and the distal end of the one or more imaging fibers 20a are connected by a transparent adhesive. Further, a non-transparent adhesive is applied on the radially outer surface of the lens 25 and also on the radially outer surface of the distal portion 20a' of the one or more imaging fibers 20a, and a first tube 36 is slid thereover to cure the adhesive and to further bond the lens 25 to the distal end of the one or more imaging fibers 20a. Then, a non-transparent adhesive is applied on the radially outer surface of the first tube 36, and a second tube 38 is slid over both the first tube 36 and the one or more imaging fibers 20a. The one or more illumination fibers 20b are arranged radially outward of the second tube 38 and are impregnated with a transparent adhesive. A protecting tube 40 is then slid over the length of the impregnated illumination fibers 20b. In one embodiment, the diameter of the lens 25 is 0.35 mm and the overall diameter of the fiber optic cable 20 is 0.78 mm, though the various dimensions of the fiber optic cable 20 are not so limited as should be apparent to one skilled in the art. A suitable fiber optic cable of this type for use in the present invention is available from POLYDIAGNOST GmbH of Germany (www.polydiagnost.com). It should be understood that other types of fiber optic cables having light illumination and image transmission capacities may also be used, as will be apparent to one skilled in the art.

While the illustrated embodiment includes the lens 25 to focus an image for transmission through the one or more imaging fibers 20a, a lens may be omitted in some applications. For example, the distal ends of the one or more imaging fibers 20a themselves may be tapered so as to internally focus an image without an additional lens.

Figure 4:
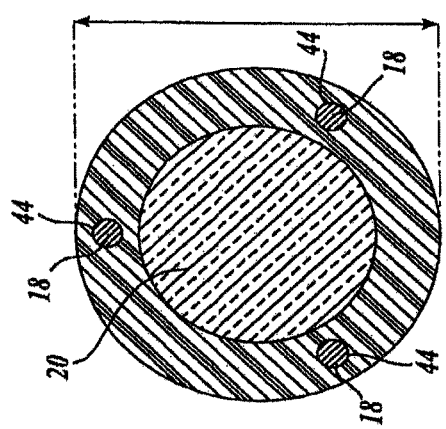
FIG. 4 is a radial cross sectional view of a catheter tube including three steering cables, formed in accordance with an embodiment of the present invention.

Referring again to FIGS. 2, 2A, 2B, and 3, the catheter tube 12 according to one embodiment of the present invention includes a lumen 42 extending axially centrally therethrough for receiving the fiber optic cable 20. In the illustrated embodiment, the cylindrical wall portion of the catheter tube 12 surrounding the lumen 42 defines four channels 44 that extend axially through the catheter tube 12. Each channel 44 receives a steering cable 18. In the illustrated embodiment, the four channels 44 are equiangularly provided along the periphery of the catheter tube 12, though the arrangement of the channels 44 may vary depending on each application. Further alternatively, referring to FIG. 4, three channels 44 may be provided, perhaps also equiangularly as illustrated, for each receiving a steering cable 18. Still alternatively, only one or two channels 44 may be provided, or five or more channels 44 may be provided for each receiving a steering cable 18, depending on the degree of maneuverability of the distal end 16 of the catheter tube 12 as required in each application.

The steering cables 18 extend freely through the channels 44 from the proximal end 14 to the distal end 16 of the catheter tube 12. Alternatively, the channels 44 may extend only partially, for example to a position near the distal end 16 of the catheter tube 12 to ensure a fixed spacing between the steering cables 16 at the distal end 16. In such a case, the steering cables 18 toward the proximal end 14 of the catheter tube 12 may extend freely through a generally annular space around the fiber optic cable 20 (without being confined within any channels 44). In any case, the distal ends of the steering cables 18 are secured to the distal end 16 of the catheter tube 12 using suitable means, such as by adhesive, soldering, anchoring, or by using a suitable fastener.

Referring back to FIG. 1, an embodiment of the control housing 26 including various electromechanical actuating elements for controlling (i.e., pulling and releasing) the steering cables 18a is illustrated. The housing 26 includes four actuators, such as servo motors 46 each coupled to a spool (not shown) adopted to be secured to the proximal end of a steering cable 18. The servo motors 46 can be selectively activated to rotate the spool in either direction so as to wind up or release the steering cable 18. If three steering cables 18 are used, then three servo motors 26 may be used. Further alternatively, only one servo motor may be used to control two steering cables that are wound in two opposite directions on a single spool. In this case, two servo motors 26 may be used to control total four steering cables 18. The servo motors 46 are controlled by a servo controller 48 which, via a controller interface 50, receives control signals from the handheld controller 27. In one embodiment, the handheld controller 27 may be formed as a joystick, which an operator can tilt in the direction in which the operator wants the distal end 16 of the catheter tube 12 to tilt. Alternatively, the handheld controller 27 may be formed of operable buttons, knobs, dials, switches, or a computer keyboard. Using the handheld controller 27, the operator can maneuver the distal end 16 of the catheter tube 12 within the patient's body cavity, while at the same time observing the image received at the distal end 16 of the catheter tube 12, either directly via the eyepiece 23 or indirectly on the screen (not shown). Some examples of the configuration and operation of a cable control system using the servo motors 46 are disclosed in co-pending U.S. patent application Ser. Nos. 10/406,149, filed Apr. 1, 2003, and Ser. No. 10/811,781, filed Mar. 29, 2004, which are incorporated herein by reference. Alternatively to the embodiments using the servo motors 46, the steering cables 18 may be manipulated by various other mechanisms including, but not limited to, linear actuators, cams, torsion-application means, etc. Further alternatively, the steering cables 18 may be manually manipulated, as in manipulating a puppet, though a manual operation may be often cumbersome and thus may not be desirable.

Regardless of the particular means employed to control the steering cables 18, pulling one of the steering cables 18 results in the distal end 16 of the catheter tube 12 to bend in the direction of the pulled steering cable 18, while releasing this steering cable 18 results in the distal end 16 of the catheter tube 12 to return to its normal position (shape). Therefore, by selectively pulling (or releasing) each of the steering cables 18 at their proximal ends, using the handheld controller 27 for example, a physician can have the distal end 16 of the catheter tube 12 to bend (or bow) in various directions and in varying degrees. This permits a physician to better control the maneuvering of the catheter tube 12 and hence the imaging catheter 10 through a tortuous pass in the body cavity, without unduly twisting and damaging the fiber optic cable 20. Further, the use of multiple cables to control the distal end significantly increases the range of view of the fiber optic cable 20.

The catheter tube 12 is formed of any suitable flexible material including, but not limited to, extruded plastic such as polytetrafluoroethylene (PTFE, Teflon®), polyether block amide, nylon, or a combination or blend of these. If strength is required, the catheter tube 12 may be formed of, or may be reinforced by including an additional layer formed of, over-extruded plastic, metal coil, mesh, stainless steel hypotube, etc. According to a preferred embodiment of the present invention, the distal portion of the catheter tube 12 (approximately 1-2 inches where the flexing occurs) is made more flexible (i.e., less stiff) than the remainder of the catheter tube 12. This serves to concentrate the flexing at the distal end portion rather than throughout the entire catheter tube, to achieve the desired motion (steering) of the catheter tube 12 while minimizing undue twisting of the entire catheter tube. Varying flexibility can be provided by various methods, such as by varying the durometer rating of materials that form the catheter tube 12, by varying the spacing between components (e.g., coil rings) that form or reinforce the catheter tube 12 along the length of the tube 12, etc. For example, by arranging coil rings relatively far apart from each other at a distal end portion of a catheter tube while arranging coil rings closer together in the remainder of the tube, a catheter tube having increasing flexibility toward its distal end can be obtained. In some embodiments, the flexibility may be varied along the length of a tube in two stages to form a tube consisting of a more flexible distal end portion and a less flexible remainder portion. In other embodiments, the flexibility may be varied gradually (e.g., increasingly) throughout the length of a catheter tube from its proximal end to its distal end. Some methods of varying the flexibility (or stiffness) of a catheter tube along its length are described in detail in U.S. patent application Ser. Nos. 10/406,149 and 10/811,781, incorporated above.

The catheter tube having varying flexibility may be used in combination with two or more steering wires to control the distal end thereof. Alternatively, it may be used with a single steering wire, and still achieves desired control of the distal end thereof while minimizing undue twisting of the entire length of the tube.

According to some embodiments of the present invention, the overall diameter of the steerable imaging catheter 10 is from about 1.0 mm to about 4.5 mm. This range is comparable to the diameter of a conventional therapeutic/diagnostic catheter and is smaller than that of a conventional endoscope, to permit visualization of a body cavity/lumen that typically cannot be reached by an endoscope.

In one embodiment, the catheter tube 12 may be manufactured specifically to be disposable, using relatively inexpensive plastic material such as medical grade polyurethane. A disposable catheter tube is advantageous in that no sterilization of a catheter is required after each use. Once a surgical operation is completed, the fiber optic cable 20 (reusable) may be simply removed from the catheter tube 12 and the catheter tube 12 (perhaps including the steering cables 18) may be discarded. In order to protect and isolate the reusable fiber optic cable 20 from external elements during use, the distal end 16 of the disposable catheter tube 12 may include a transparent sealing cover.

According to one embodiment of the present invention, the exterior surface of the catheter tube 12 may be coated with lubricous, for example hydrophilic material so as to facilitate the placement of the catheter tube 12 inside a patient's anatomy. Additionally or alternatively, the exterior surface of the fiber optic cable 20 may be coated with lubricous, hydrophilic material so as to reduce friction and facilitate the placement of the fiber optic cable 20 through the catheter tube 12, in particular when the fiber optic cable 20 (reusable) is to be used with a disposable catheter tube 12, as described above. In some applications, hydrophilic material should be reusable so as to retain its hydrophilic properties through multiple uses (and perhaps also to withstand sterilization at least for several times). Suitable hydrophilic coating material includes polytetrafluoroethylene (PTFE) based material, such as those available under the trademarks of Hydropass™ and Endoglide™ from Boston Scientific Corporation of Natick, Mass. (www.bsci.com), described in U.S. Pat. Nos. 5,702,754 and 6,048,620, which are herein incorporated by reference. The thickness of the coating on the fiber optic cable 20 must be thin enough to permit the fiber optic cable 20 to pass through the catheter tube 12 having a specific diameter (which in turn is limited by the dimensions of the patient's anatomy), and at the same time must be thick enough to withstand abrasion and other damages. The thickness of the coating on the catheter tube 12 may be similarly determined. Coating may be applied using various methods as will be apparent to one skilled in the art, such as by dipping the fiber optic cable 20 (or the catheter tube 12) in the coating material, or spraying, painting, or printing the coating material on the fiber optic cable 20 (or the catheter tube 12).

According to one embodiment of the present invention, the fiber optic cable 20 is integrally formed with the catheter tube 12 by various means, such as by over-extruding a plastic material over the fiber optic cable 20, by adhesive, or by heat-shrinking the catheter tube 12 around the fiber optic cable 20. This will prevent removal of the fiber optic cable 20 from the catheter tube 12, which may be desirable in some applications. In such an embodiment, the distal end(s) of one or more control cables 18 may be attached directly to the distal, end of the fiber optic cable 20. If the catheter tube 12 is intended to be disposable, as described above, then the fiber optic cable 20 integrally formed therein will also be discarded together with the catheter tube 12 after each use. Alternatively, the catheter tube 12 integrally including the fiber optic cable 20 may be built for repeated use and sterilization.

Figure 5:
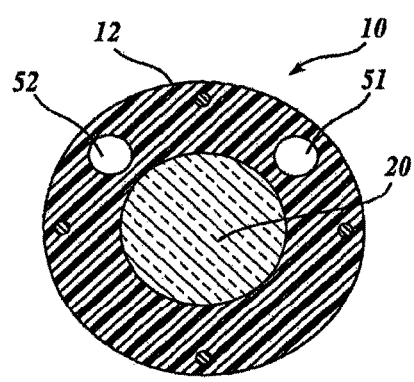
FIG. 5 is a radial cross sectional view of a catheter tube including two additional lumens, formed in accordance with the present invention.

Referring to FIG. 5, the catheter tube 12 of the steerable imaging catheter 10 may further include one or more additional lumens 51, 52 to axially extend therethrough. These additional lumens 51, 52 may receive any fluid (for irrigation and sufflation purposes, for example), or other devices and equipment, such as a cutting device including a cold cutting device and a cutting wire that delivers RF energy. The deployment of any of these additional devices and equipment may also be controlled by the handheld controller 27, or may be independently controlled, as should be apparent to one skilled in the art.

Figure 6:
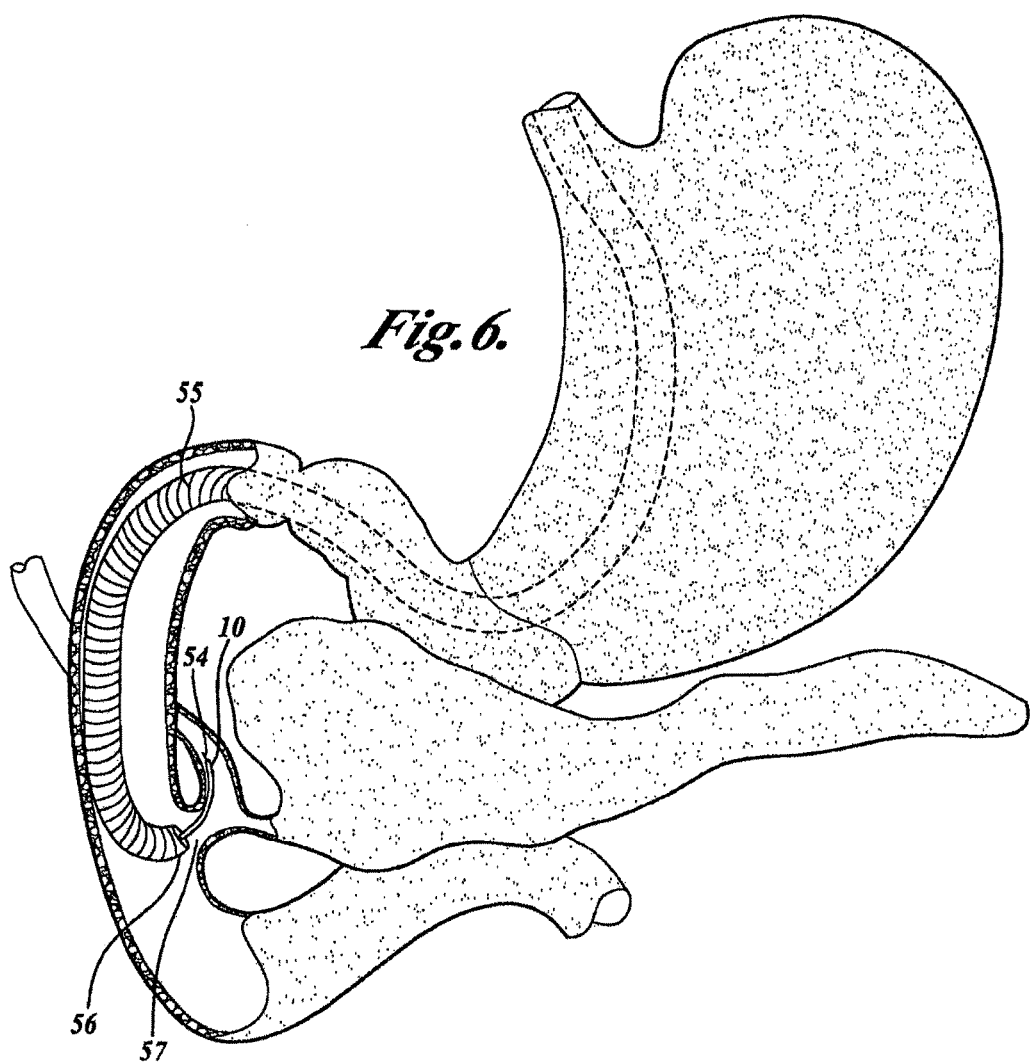
FIG. 6 is a schematic view of the billary system in which a steerable imaging catheter of the present invention is introduced via an endoscope.

For example, referring to FIG. 6, the steerable imaging catheter 10 including an additional lumen (51 or 52) through which a cutting wire 54 extends, is used in conjunction with an endoscope (e.g., duodenoscope) 55. The endoscope 55 is advanced into a patient's billary system until the distal end 56 thereof is positioned near the sphincter of oddi within the duodenum (at the bottom of the stomach), as illustrated. Then, a physician advances the steerable imaging catheter 10 of the present invention through a lumen of the endoscope 55 and through the sphincter to enter the common bile duct and pancreatic duct 57, perhaps by manipulating the handheld controller 27 to controllably bend the distal end 16 of the catheter tube 12. Once in place in the bile duct, a physician deploys the cutting wire 54 at the distal end 16 of the catheter tube 12. The cutting wire 54 delivers RF energy to the tissue in order to cut the sphincter, thereby allowing the removal of stones or other objects from the patient's gallbladder. At the same time, the fiber optic cable 20 within the imaging catheter 10 allows a physician to view tissue further in the bile duct for diagnosis or treatment. In this regard, according to one embodiment of the present invention, the fiber optic cable 20 freely extends through the lumen 42 of the catheter tube 12 so as to extend (or protrude) further from the distal end 16 of the catheter tube 12, to thereby additionally advance into a smaller-diameter area. The deployment of the fiber optic cable 20 may also be controlled by the handheld controller 27, or may be independently controlled, as should be apparent to one skilled in the art. In this configuration, a tapered system is formed starting with the endoscope 55, which slidably includes the steerable imaging catheter 10, which in turn slidably includes the fiber optic cable 20.

In one embodiment, one of the steering cables 18 may additionally serve as the cutting wire for delivering RF energy. In this embodiment, the distal end portion of the steering cable 18 is exposed to the outside of the catheter tube 12 so as to be able to contact the undesirable material to be removed.

A steerable imaging catheter of the present invention may be passed through a working lumen of an endoscope, as described above, or may be passed through a working lumen of a non-endoscope device (e.g., biopsy forceps). Further-more, a steerable imaging catheter of the present invention may be introduced into a body cavity of a patient adjacent to a non-endoscope device, either completely separately, or in combination such as by a snap-on type bracket provided on the side of the non-endoscope device that contains but not necessarily constrains the steerable imaging catheter.

Figure 7:
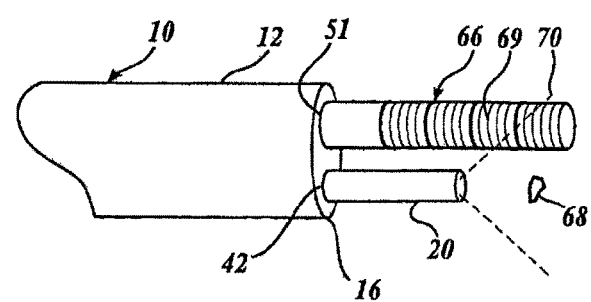
FIG. 7 illustrates a steerable imaging catheter of the present invention used in conjunction with a measuring probe for measuring the size or distance of object(s) in the field of view.

The one or more additional lumens 51, 52 provided through a catheter tube 12 of an imaging catheter 10 may also receive a measuring probe. FIG. 7 illustrates that the additional lumen 51 slidably receives an elongated measuring probe 66. As before, the lumen 42 of the catheter tube 12 receives the fiber optic cable 20 therethrough, although in the illustrated embodiment the lumen 42 is not centrally defined through the catheter tube 12 unlike in the previously described embodiments. The measuring probe 66 is used in conjunction with the fiber optic cable 20 to measure the size or distance of objects within the patient's anatomy, such as the size of stones, sphincters, or tissue (a stone 68 is shown in FIG. 7). To this end, the measuring probe 66 includes high-contrast, perhaps color-coded incremental or numerical markings 69 at its distal end portion. Different types of markings will indicate distance such as larger marks for significant distances and smaller marks for lesser distances. Also, alternate colors may be used to identify specific distances. For example, a green band may be 1 mm wide, followed by a red band that is also 1 mm wide. This would allow the observer to readily see the 2 mm total transition from 1 mm-red to 1 mm-green and estimate the total distance accordingly. The markings 69 may also include spots or dots that are of specific diameters or distances from one another. Additionally or alternatively, the markings 69 may indicate a specific size/distance, which readily indicates to a physician that anything bigger than (or smaller than) this specific size/distance is of concern, for example. Further alternatively, the markings 69 may be in the form of a spiral/helical pattern so that, when they are axially moved, they readily indicate the direction of movement to the observing physician.

The probe 66 may be made of any suitable material flexible enough to pass through a patient's anatomy and yet rigid enough to permit reading of the markings 69.

The incremental markings 69 provide a reference against which an object (e.g., stone 68) in the viewing field of the steerable imaging catheter 10 can be compared. Specifically, in operation, a physician places the incremental markings 69 provided at the distal portion of the measuring probe 66 relative to the fiber optic cable 20 so that both the object (e.g., stone) 68 and the markings 69 will be in the field of view 70. Then, the physician, using the fiber optic cable 20, visually measures the size of the object 68 in reference to the incremental markings 69 of the measuring probe 66. In this regard, in order to deliver the fiber optic cable 20 and the measuring probe 66 generally in tandem to the body cavity of interest, as illustrated, one embodiment of the catheter tube 12 defines two lumens arranged in a generally side-by-side configuration: the lumen 42 for receiving the fiber optic cable 20; and the additional lumen 51 for receiving the measuring probe 66. In one embodiment, to strictly maintain the tandem configuration, both the fiber optic cable 20 and the measuring probe 66, in a relative tandem configuration, may be fixedly secured in the catheter tube 12. Alternatively, in another embodiment, the fiber optic cable 20 and/or the measuring probe 66 freely extend through the catheter tube 12.

In accordance with one embodiment, the fiber optic cable 20 itself may be provided with the markings 69 near its distal end, which can then be viewed by another device having imaging capability (e.g., another fiber optic cable 20). Alternatively, the markings 69 may be provided on a portion of the fiber optic cable 20 near its proximal end, which does not enter the patient's body. In this embodiment, a physician can measure a distance/size by directly counting the proximal markings 69 (outside the patient's body) while inserting or pulling the fiber optic cable 20 in and out of the patient.

In accordance with one embodiment of the present invention, the fiber optic cable 20 may be configured to transmit electromagnetic energy (including both visible and non-visible ranges) for further diagnosis/treatment purposes. For example, to perform an optical biopsy, a suitable diagnostic system. (72 in FIG. 1) is provided, including software for processing the signals received via the fiber optic cable 20 to make a diagnosis. As a specific example, based on the fact that cancerous and necrotic tissue has a different density and thus absorbs a different wavelength of light than healthy tissue, the fiber optic cable 20 can be used to irradiate light of a certain wavelength range on the tissue in question, and then to read the light reflected back from the tissue. The diagnostic system 72 contains software to subtract the reflected light from the irradiated light to determine the wavelength of the light that was absorbed by the tissue, thereby making a diagnosis of the tissue. Other optic-based diagnostic techniques may also be used with the fiber optic cable 20, as should be apparent to one skilled in the art, such as interferometry, induced or natural fluorescence, and Rayleigh scattering. Another example of a suitable technique is the laser Raman spectroscopy as applied in tissue or bloodstream. Specifically, a given tissue will have signature intensity peaks at a specific Raman shift interval or range of intervals. Mapping or scanning known healthy tissue for Raman shift to develop a database for comparison will enable clinicians to compare an arbitrary Raman scan of tissue for abnormalities. Similarly, Raman scans of known unhealthy or cancerous tissues may be used to be compared to an arbitrary Raman scan to predict disease state (malignant or benign). The prediction may aid in the decision to take tissue samples for further testing. Any optical biopsy method can be used to make instant diagnosis of tissue without having to remove a biopsy sample of tissue from the patient.

While the preferred embodiments of the invention have been illustrated and described, it will be appreciated that various changes can be made therein without departing from the scope of the invention.

The embodiments of the invention in which an exclusive property or privilege is claimed are defined as follows:
1. An imaging system, comprising:
    an introducer, including:
        a sheath having a lumen,
        a proximal opening at a proximal end of the lumen, and
        a distal opening at a distal end of the lumen;
    an imaging device for insertion into the introducer, the imaging device including a shaft, the shaft including:
        imaging fibers for transmitting an image proximally along the shaft,
        a lens distal to a distal end portion of the imaging fibers,
        a first tube coupled to the lens and extending concentrically around the lens, wherein the first tube and the distal end portion of the imaging fibers have the same circumference,
        illumination fibers for transmitting light distally along the shaft, the illumination fibers extending concentrically around the imaging fibers, and a sheath extending concentrically around the illumination fibers, wherein the imaging device is longer than the introducer.

2. The imaging system of claim 1, wherein the introducer further includes:
   at least one steering wire extending through the sheath, and
   a deflection controller for exerting a force on the at least one steering wire to deflect a distal end of the sheath.

3. The imaging system of claim 2, wherein the deflection controller is proximal to the proximal opening.

4. The imaging system of claim 1, wherein a central longitudinal axis of the proximal opening is angled relative to a central longitudinal axis of the sheath.

\* \* \* \* \*